US009649167B2

(12) United States Patent
Miyamoto

(10) Patent No.: US 9,649,167 B2
(45) Date of Patent: May 16, 2017

(54) PATTERN AND SURGERY SUPPORT SET, APPARATUS, METHOD AND PROGRAM

(71) Applicant: FUJIFILM Corporation, Tokyo (JP)

(72) Inventor: Masaki Miyamoto, Tokyo (JP)

(73) Assignee: FUJIFILM CORPORATION, Tokyo (JP)

( * ) Notice: Subject to any disclaimer, the term of this patent is extended or adjusted under 35 U.S.C. 154(b) by 283 days.

(21) Appl. No.: 14/270,177

(22) Filed: May 5, 2014

(65) Prior Publication Data

US 2014/0333617 A1 Nov. 13, 2014

(30) Foreign Application Priority Data

May 8, 2013 (JP) ................................. 2013-098424

(51) Int. Cl.
G06T 17/00 (2006.01)
A61B 19/00 (2006.01)
A61B 34/10 (2016.01)
A61B 90/00 (2016.01)

(52) U.S. Cl.
CPC .............. *A61B 19/50* (2013.01); *A61B 34/10* (2016.02); *A61B 2034/104* (2016.02); *A61B 2034/105* (2016.02); *A61B 2034/108* (2016.02); *A61B 2090/378* (2016.02); *A61B 2090/3908* (2016.02); *A61B 2090/3937* (2016.02)

(58) Field of Classification Search
None
See application file for complete search history.

(56) References Cited

U.S. PATENT DOCUMENTS

| 5,768,134 | A  | * | 6/1998  | Swaelens   | A61C 13/0004 433/201.1 |
|-----------|----|---|---------|------------|------------------------|
| 6,304,770 | B1 |   | 10/2001 | Lee et al. |                        |
| 9,179,914 | B2 | * | 11/2015 | Belson     | A61B 17/08             |
| 2002/0143326 | A1 | * | 10/2002 | Foley    | A61B 18/1492 606/41   |
| 2003/0182815 | A1 |   | 10/2003 | Carlson, II |                      |

(Continued)

FOREIGN PATENT DOCUMENTS

| EP | 1004274 A1 | 5/2000 |
|----|------------|--------|
| EP | 2422736 A2 | 2/2012 |

(Continued)

OTHER PUBLICATIONS

Extended European Search Report dated Jan. 20, 2015.

*Primary Examiner* — Frank Chen
(74) *Attorney, Agent, or Firm* — McGinn IP Law Group, PLLC.

(57) ABSTRACT

A three-dimensional image representing a patient's organ is obtained. The organ is extracted from the three-dimensional image. A treatment portion, at which desirable treatment for the organ is performed, on a surface of the organ is obtained. A pattern model including an outer surface, an inner surface having a surface form along an organ's outer surface of the organ, a guide wall connecting, along the treatment portion, the outer surface and the inner surface, and a positioning portion is generated. The positioning portion positions a predetermined imaging probe in such a manner that a tomographic image of a cross section of the organ including a target portion of the organ is imageable when the guide wall is arranged along the treatment portion on the organ.

10 Claims, 9 Drawing Sheets

(56) References Cited

U.S. PATENT DOCUMENTS

| | | | |
|---|---|---|---|
| 2004/0092815 A1* | 5/2004 | Schweikard | A61B 6/12 600/425 |
| 2005/0049486 A1* | 3/2005 | Urquhart | A61B 34/20 600/429 |
| 2006/0020204 A1* | 1/2006 | Serra | A61B 8/0833 600/437 |
| 2009/0024030 A1* | 1/2009 | Lachaine | A61B 8/0825 600/437 |
| 2011/0093108 A1 | 4/2011 | Ashby et al. | |

FOREIGN PATENT DOCUMENTS

| | | |
|---|---|---|
| EP | 2687168 A1 | 1/2014 |
| JP | 2000-157554 A | 6/2000 |
| JP | 2001-283191 A | 10/2001 |
| JP | 2003-33349 A | 2/2003 |
| JP | 2005-521460 A | 7/2005 |
| JP | 2011-517579 A | 6/2011 |
| JP | 2011-172977 A | 9/2011 |

* cited by examiner

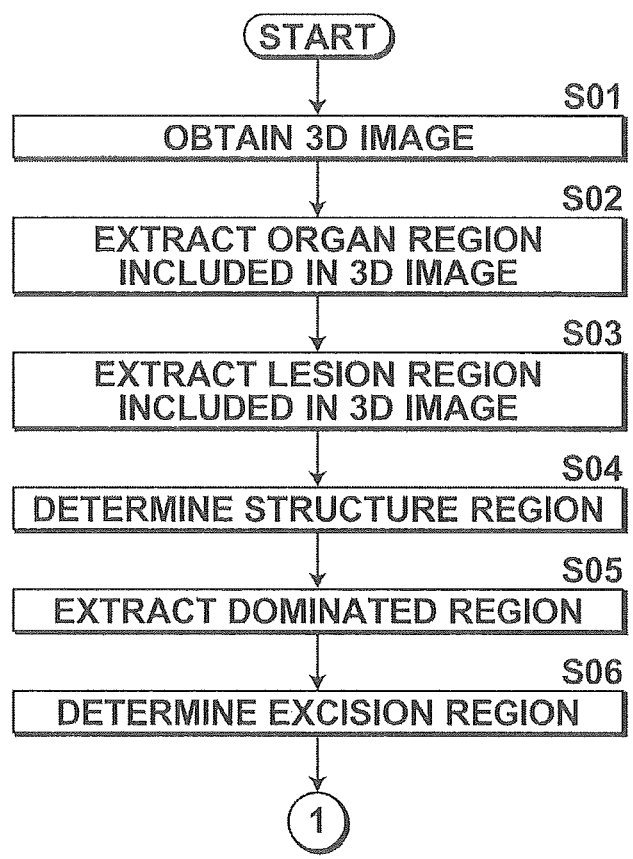

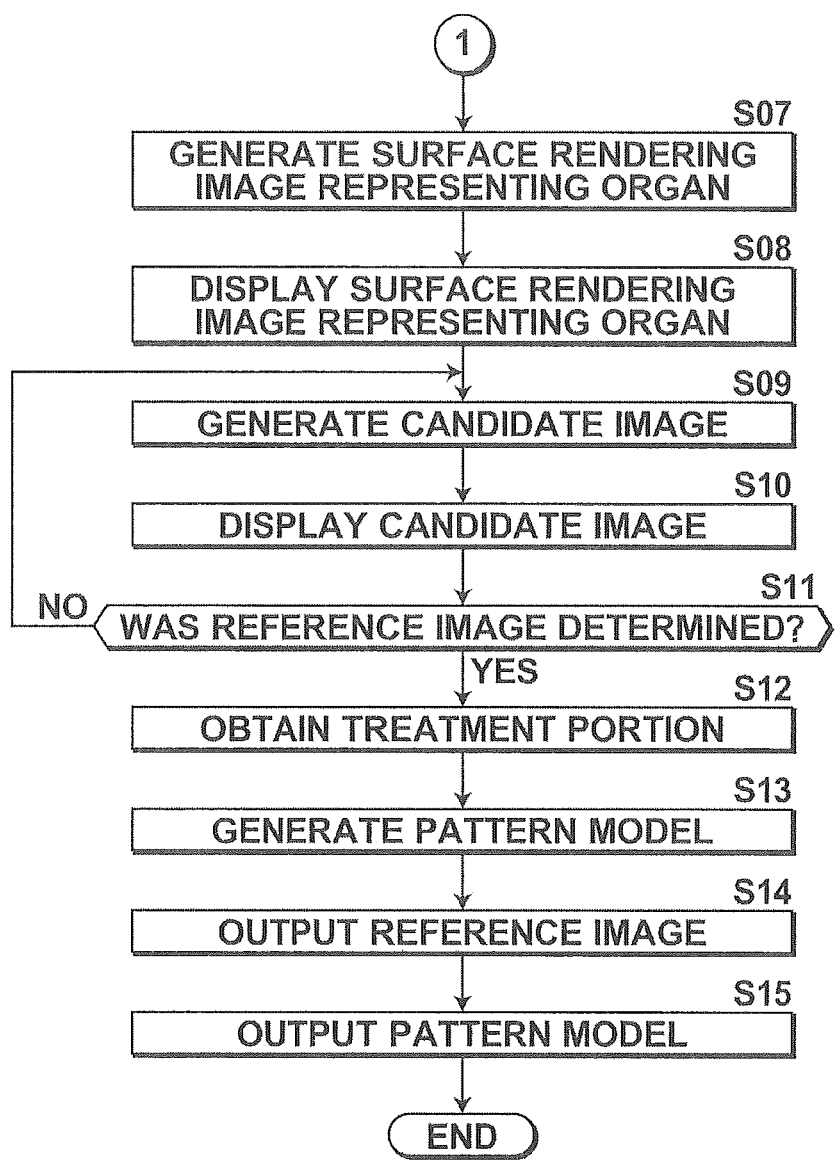

PATTERN AND SURGERY SUPPORT SET, APPARATUS, METHOD AND PROGRAM

BACKGROUND OF THE INVENTION

Field of the Invention

The present invention relates to a pattern for supporting surgery by guiding a treatment position at which treatment is performed on an organ in surgery of the organ, and to a surgery support set, and to a surgery support apparatus, method and program.

Description of the Related Art

When surgery, such as excision of a part of a patient's organ, is performed, doctors determine an excision portion of the organ so as to include a lesion by checking the form of the organ and the position of the lesion in diagnosis using images before the surgery. Further, the doctors need to appropriately recognize, based on the determined excision portion, a treatment portion on a surface of the organ at which treatment, such as excision, should be performed, and to perform treatment, such as excision at the treatment portion.

Japanese Unexamined Patent Publication No. 2011-172977 (Patent Document 1) and PCT Japanese Publication No. 2011-517579 (Patent Document 2) propose bone templates to make such a treatment portion easily recognizable. The bone template is engageable with a characteristic portion of a bone in surgery. Further, an excision line of the bone is a slit in the bone template. Japanese Unexamined Patent Publication No. 2000-157554 (Patent Document 3) discloses an apparatus that stably supports a surgery-target region (breast). The apparatus includes an opening part for observation by an ultrasonic apparatus and an opening part provided at a position corresponding to an incision portion. Incision is performed on the breast at the opening part of the apparatus, and an ultrasonic transducer is inserted into the breast through the incision portion, and an affected region is observed. PCT Japanese Publication No. 2005-521460 (Patent Document 4) discloses a transparent film indicating a surgical treatment position.

SUMMARY OF THE INVENTION

However, the techniques disclosed in Patent Documents 1, 2 and 4 have a problem that it is difficult to know a place at which a template of an organ or a transparent film should be arranged only based on external characteristics of the organ, for example, when the organ is a liver or the like. Meanwhile, Patent Document 3 discloses the technique for partially removing the inside of the breast by inserting a treatment tool through an incision portion of the breast after the breast, on which surgery is to be performed, is deformed to be in close contact with the apparatus and stabilized. Therefore, the technique disclosed in Patent Document 3 does not satisfy a need for arranging, at an appropriate position of the organ, a pattern indicating a treatment portion on a surface of the organ, which is set at a different position based on the position of the lesion and the purpose of treatment.

In view of the foregoing circumstances, it is an object of the present invention to provide a pattern, a surgery support set and a surgery support apparatus, method and program for supporting an operation for positioning a pattern indicating a treatment portion on a surface of an organ at an appropriate position on the organ.

A surgery support apparatus of the present invention is a surgery support apparatus comprising:

an image obtainment unit that obtains a three-dimensional image representing a patient's organ;

an organ extraction unit that extracts the organ from the three-dimensional image;

a treatment portion obtainment unit that obtains a treatment portion, at which desirable treatment for the organ is performed, on a surface of the organ; and a pattern model generation unit that generates, based on the extracted organ and the obtained treatment portion, a pattern model including an outer surface, an inner surface having a surface form along an organ's outer surface of the organ, a guide wall connecting, along the treatment portion, the outer surface and the inner surface, and a positioning portion that positions a predetermined imaging probe in such a manner that a tomographic image of a cross section of the organ including a target portion of the organ is imageable when the guide wall is arranged along the treatment portion on the organ.

A surgery support method of the present invention is a surgery support method performed by a surgery support apparatus, the method comprising the steps of:

image obtainment to obtain a three-dimensional image representing a patient's organ;

organ extraction to extract the organ from the three-dimensional image;

treatment portion obtainment to obtain a treatment portion, at which desirable treatment for the organ is performed, on a surface of the organ; and pattern model generation to generate, based on the extracted organ and the obtained treatment portion, a pattern model including an outer surface, an inner surface having a surface form along an organ's outer surface of the organ, a guide wall connecting, along the treatment portion, the outer surface and the inner surface, and a positioning portion that positions a predetermined imaging probe in such a manner that a tomographic image of a cross section of the organ including a target portion of the organ is imageable when the guide wall is arranged along the treatment portion on the organ.

A surgery support program of the present invention is a surgery support program for causing a computer to function as:

an image obtainment unit that obtains a three-dimensional image representing a patient's organ;

an organ extraction unit that extracts the organ from the three-dimensional image;

a treatment portion obtainment unit that obtains a treatment portion, at which desirable treatment for the organ is performed, on a surface of the organ; and a pattern model generation unit that generates, based on the extracted organ and the obtained treatment portion, a pattern model including an outer surface, an inner surface having a surface form long an organ's outer surface of the organ, a guide wall connecting, along the treatment portion, the outer surface and the inner surface, and a positioning portion that positions a predetermined imaging probe in such a manner that a tomographic image of a cross section of the organ including a target portion of the organ is imageable when the guide wall is arranged along the treatment portion on the organ.

A pattern of the present invention is a pattern comprising:

an outer surface;

an inner surface having a surface form along an organ's outer surface of a patient's organ;

a guide wall connecting, along a treatment portion at which desirable treatment for the organ is performed on a surface of the organ, the outer surface and the inner surface; and a positioning portion that positions a predetermined imaging probe in such a manner that tomography of a cross section of the organ including a target portion of the organ is performable when the guide wall is arranged along the treatment portion on the organ.

A surgery support set of the present invention is a surgery support set comprising:

the pattern; and a reference image that has been output in such a manner that a tomographic image of a cross section of the patient's organ including the target portion is visually recognizable, wherein the positioning portion of the pattern is structured in such a manner that tomography of the cross section of the organ represented in the reference image is performable by the imaging probe positioned by the positioning portion when the guide wall is arranged along the treatment portion on the organ.

The "positioning portion" should be structured in such a manner that an imaging probe is positionable. For example, the positioning portion may be structured to include a wall that abuts on an outer surface of the imaging probe. In this case, it is desirable that the positioning portion includes a wall that abuts on the outer surface of the imaging probe at different angles, and that connects the outer surface and the inner surface. Here, the expression that the wall "that abuts on the outer surface of the imaging probe at different angles" means that normals to tangent planes at two of contact points of the wall and the outer surface of the imaging probe have different angles from each other.

Further, the "target portion" should be a characteristic portion, which is usable as a mark by which a relative position with respect to an organ is recognizable. For example, a part of an anatomical structure, such as a branching point of blood vessels in an organ, a lesion region and an outline of an organ may be used as the target portion.

In the present invention, the positioning portion may be a hole extending through the pattern model from the inner surface to the outer surface, and through which an imaging probe is insertable and detachable. In this case, for example, the hole may be structured so as to have substantially the same form as the form of the outer surface of the imaging probe, thereby the hole and the outer surface of the imaging probe becoming substantially in close contact with each other. In this manner, positioning of the imaging probe becomes possible.

Further, it is desirable that the pattern model generation apparatus of the present invention further includes an image generation unit that generates a reference image, which is a tomographic image of the cross section of the organ including the target portion of the organ, from the three-dimensional image.

Further, the pattern model generation apparatus of the present invention may further include a reference image determination unit that determines the reference image from a plurality of candidate images, and a display control unit that displays the reference image on a display device. Further, the image generation unit may generate, based on the three-dimensional image, a plurality of candidate images that are tomographic images representing different cross sections of the organ, respectively. Further, the display control unit may display the generated plurality of candidate images on the display device. Further, the reference image determination unit may determine, as the reference image, a candidate image specified by a user by receiving specification of determining the displayed candidate image as the reference image by the user.

In the pattern model generation apparatus of the present invention, the pattern model may include a guide hole extending through the pattern model from the outer surface to the inner surface, and the guide hole may include a guide wall provided on both sides of the treatment portion.

In the pattern model generation apparatus of the present invention, the guide wall may be provided on an edge of the pattern model.

In the pattern model generation apparatus of the present invention, the imaging probe may be an ultrasonic probe.

According to the pattern of the present invention, the pattern includes an outer surface, an inner surface having a surface form along an organ's outer surface of a patient's organ, a guide wall connecting, along a treatment portion at which desirable treatment for the organ is performed on a surface of the organ, the outer surface and the inner surface, and a positioning portion that positions a predetermined imaging probe in such a manner that tomography of a cross section of the organ including a target portion of the organ is performable when the guide wall is arranged along the treatment portion on the organ. Therefore, it is possible to easily arrange the pattern at an appropriate position on the organ by arranging the pattern on the surface of the organ in such a manner that a tomographic image imaged from the imaging probe positioned by the positioning portion is a tomographic image including the target portion.

According to the surgery support set of the present invention, the surgery support set includes the pattern, and a reference image that has been output in such a manner that a tomographic image of a cross section of the patient's organ including the target portion is visually recognizable. Further, the positioning portion of the pattern is structured in such a manner that tomography of the cross section of the organ represented in the reference image is performable by the imaging probe positioned by the positioning portion when the guide wall is arranged along the treatment portion on the organ. Therefore, it is possible to arrange the pattern at an appropriate position on the organ by arranging the pattern on the surface of the organ in such a manner that a tomographic image imaged from the imaging probe positioned by the positioning portion represents a cross section of the organ represented by a reference image.

According to the surgery support apparatus, the surgery support method and the surgery support program of the present invention, a three-dimensional image representing a patient's organ is obtained, and the organ is extracted from the three-dimensional image, and a treatment portion, at which desirable treatment for the organ is performed, on a surface of the organ is obtained, and a pattern model is generated based on the extracted organ and the obtained treatment portion. The pattern model includes an outer surface, an inner surface having a surface form along an organ's outer surface of the organ, a guide wall connecting, along the treatment portion, the outer surface and the inner surface, and a positioning portion that positions a predetermined imaging probe in such a manner that a tomographic image of a cross section of the organ including a target portion of the organ is imageable when the guide wall is arranged along the treatment portion on the organ. Therefore, it is possible to generate a pattern model, which is data of the pattern of the present invention. Hence, it is possible to output the pattern of the present invention based on the generated pattern model.

Note that the program of the present invention may be provided being recorded on a computer readable medium. Those who are skilled in the art would know that computer readable media are not limited to any specific type of device, and include, but are not limited to: floppy disks, CD's, RAM's, ROM's, hard disks, magnetic tapes, and Internet downloads, in which computer instructions can be stored and/or transmitted. Transmission of the computer instructions through a network or through wireless transmission means is also within the scope of this invention. Additionally, computer instructions include, but are not limited to: source, object and executable code, and can be in any language including higher level languages, assembly language, and machine language.

BRIEF DESCRIPTION OF THE DRAWINGS

FIG. 4A is a flowchart illustrating a flow of surgery support processing according to an embodiment of the present invention (No. 1);

FIG. 4B is a flowchart illustrating a flow of surgery support processing according to an embodiment of the present invention (No. 2);

DESCRIPTION OF THE PREFERRED EMBODIMENTS

Hereinafter, a surgery support apparatus, a surgery support method, a surgery support program, a pattern and a surgery support set according to embodiments of the present invention will be described in detail with reference to drawings.

In each of the following embodiments, a surgery support apparatus 1 is a computer in which a surgery support program according to each of the embodiments has been installed. The computer may be a workstation or a personal computer directly operated by a doctor who performs diagnosis, or a server computer connected to them through a network. The surgery support program may be stored in a recording medium, such as a DVD and a CD-ROM, and distributed, and installed in a computer from the recording medium. Alternatively, the surgery support program may be stored in a storage apparatus of a server computer connected to a network or a network storage in a state of being accessible from the outside. Further, the surgery support program may be downloaded in a computer used by a doctor based on a request, and installed in the computer.

Figure 1:
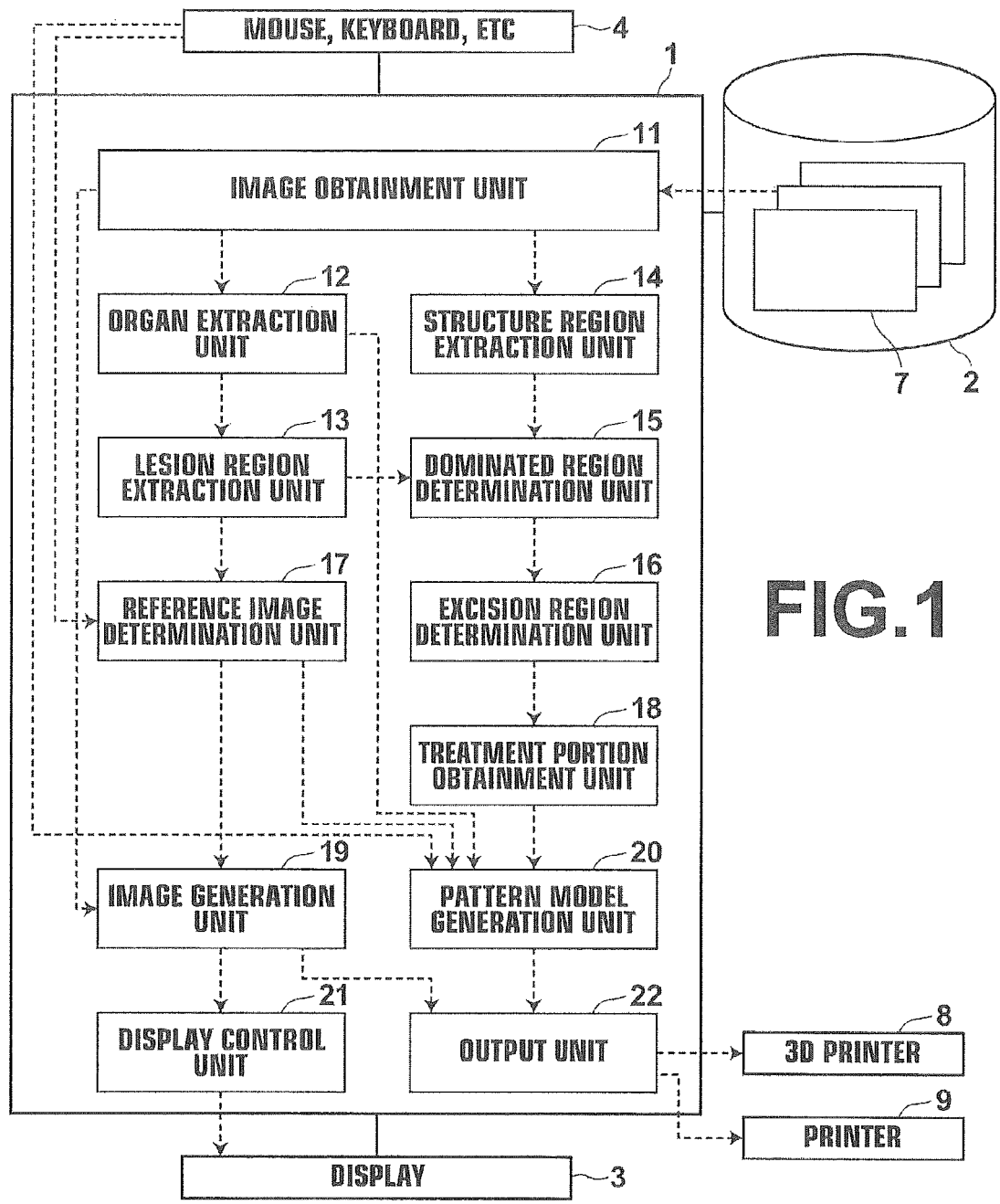
FIG. 1 is a schematic diagram illustrating the configuration of a surgery support apparatus according to an embodiment of the present invention.

FIG. 1 is a schematic diagram illustrating the configuration of a surgery support apparatus 1 realized by installing a surgery support program at a workstation. As illustrated in FIG. 1, the surgery support apparatus 1 has general workstation configuration including a CPU, which is not illustrated, and a memory, which is not illustrated. The surgery support apparatus 1 includes a storage 2. Further, a display 3, an input unit 4, such as a mouse, a three-dimensional printer 8, and a printer 9 are connected to the surgery support apparatus 1. The three-dimensional printer 8 outputs, based on three-dimensional shape data, a three-dimensional structure composed of resin or powder. The printer 9 outputs (prints), based on two-dimensional data, print content on a sheet.

The storage 2 stores, as a three-dimensional image 7, volume data obtained by imaging a patient's organ at a CT (Computed Tomography) apparatus, or the like.

The memory stores a surgery support program and data referred to by the surgery support program (a processing parameter or the like). The surgery support program defines, as processing executed by the CPU, image obtainment processing, organ region extraction processing, lesion region extraction processing, structure region extraction processing, dominated region extraction processing, excision region determination processing, reference image determination processing, treatment portion obtainment processing, pattern model generation processing, image generation processing, output processing and display control processing. When the CPU executes these kinds of processing in accordance with the program, a general-purpose workstation functions as an image obtainment unit 11, an organ region extraction unit 12, a lesion region extraction unit 13, a structure region extraction unit 14, a dominated region extraction unit 15, an excision region determination unit 16, a reference image determination unit 17, a treatment portion obtainment unit 18, a pattern model generation unit 20, an image generation unit 19, an output unit 22 and a display control unit 21, which will be described later.

Figure 2A:
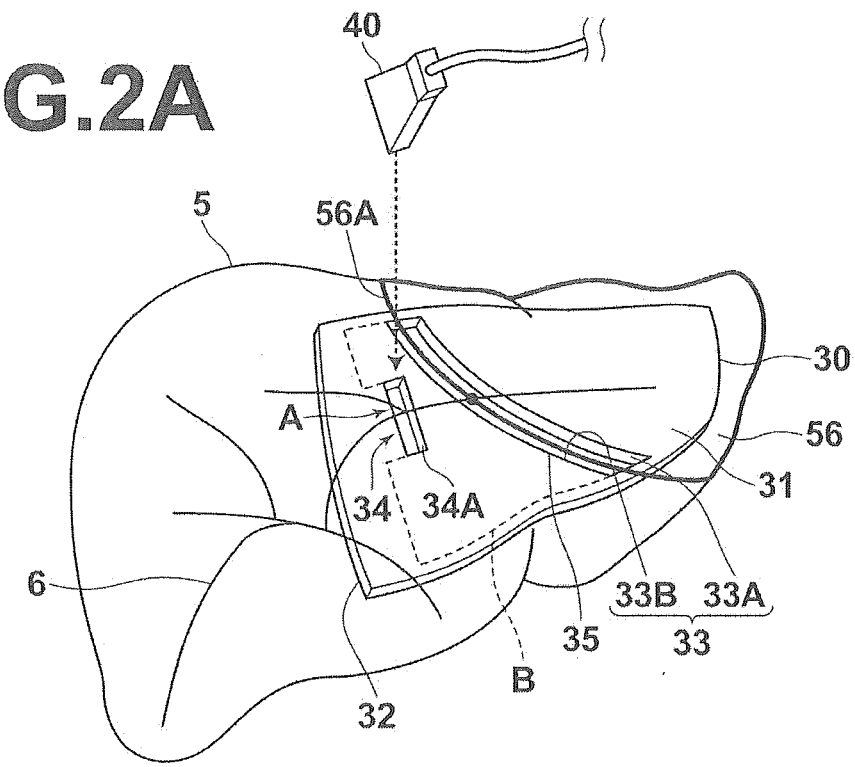
FIG. 2A is a diagram illustrating an example of a pattern according to an embodiment of the present invention.
Figure 2B:
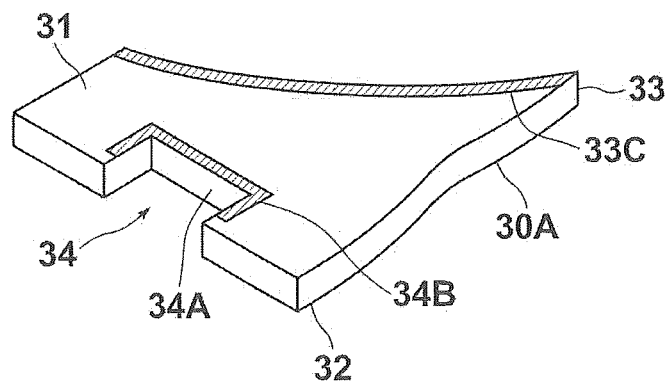
FIG. 2B is a diagram illustrating a modified example of a pattern according to an embodiment of the present invention.

First, a pattern 30 generated by the surgery support apparatus 1 according to an embodiment of the present invention will be described. FIG. 2A is a diagram illustrating the pattern 30 generated by the surgery support apparatus 1 according to an embodiment of the present invention. FIG. 2B is a diagram illustrating a pattern 30A, which is a modified example of a pattern generated by the surgery support apparatus 1 according to an embodiment of the present invention. The pattern 30A illustrated in FIG. 2B is structured to be arrangeable on broken line B on a liver 5 illustrated in FIG. 2A.

The pattern 30 according to the embodiment of the present invention includes an outer surface 31, an inner surface 32 having a surface form along an organ's outer surface of the liver 5, which is an organ, a guide wall 33 connecting, along a treatment portion 56A, the outer surface 31 and the inner surface 32, and a positioning portion 34 that positions a predetermined imaging probe 40 in such a manner that a tomographic image of a cross section of the organ including target portion A of the organ is imageable when the guide wall 33 is arranged along the treatment portion 56A on the organ (please refer to FIG. 2A). The treatment portion 56A is a boundary between an excision region 56 of the liver 5 and a non-excision region. The treatment portion 56A is an excision line on the surface of the liver, at which doctors perform incision.

The present invention is not limited to the embodiments of the present invention. A pattern of the present invention may be generated for various kinds of organ, and applied. Further, the treatment portion 56A may be a linear part, a dot-shaped part, or a closed curve part as long as treatment that physically acts on an organ is performed at the portion on the surface of the organ.

In the embodiment of the present invention, the pattern 30 has a guide hole 35 extending through the pattern 30 from the outer surface 31 to the inner surface 32. The guide hole 35 has guide walls 33A and 33B provided on both sides of the treatment portion 56A. Therefore, when the pattern 30 is positioned on the organ, doctors can easily recognize the treatment portion 56A by the guide wall 33. Further, it is possible to more accurately perform treatment on the treatment portion 56A by performing treatment along the guide hole 35.

The guide wall 33 may be provided along the entire range of the treatment portion 56A or along a part of the treatment portion 56A as long as the guide wall 33 is provided along the treatment portion 56A and connects the outer surface 31 and the inner surface 32. When the treatment portion 56A is larger than the guide hole 35 of the pattern 30, as in the embodiment of the present invention, doctors may arrange the pattern 30 on the liver 5, and perform treatment on a part of the treatment portion along the guide hole 35. Then, the doctors may remove the pattern 30 on the liver 5 therefrom, and perform the remaining treatment by using the treated part of the treatment portion, as a mark. Alternatively, doctors may arrange the pattern 30 on the liver 5, and provide, along the guide wall 33, a marking on the liver 5, and remove the pattern 30 on the liver 5 therefrom. Further, a part of the liver 5 on which marking has been provided may be treated.

The guide wall 33 may be provided at an edge of the pattern. In this case, it is possible to easily recognize the treatment portion 56A based on the guide wall 33. Further, it is possible to more accurately perform treatment on the treatment portion 56A by performing treatment along the guide wall 33. FIG. 2B illustrates an example in which the guide wall 33 is provided at an edge of the pattern.

Further, an index for identification may be provided, along the guide wall 33, near the guide wall 33 or on the guide wall 33 in such a manner that the guide wall 33 is identifiable. In FIG. 2B, a band-shaped colored portion 33C is provided along the guide wall 33 on the outer surface 31. In this case, a user can more clearly recognize the guide wall 33. Alternatively, the guide wall may be identifiably structured by using various kinds of index, such as an arrow and a character, or by using different colors.

The positioning portion 34 positions the predetermined imaging probe 40 in such a manner that a tomographic image of cross section C of the organ including target portion A in the liver 5 is imageable when the guide wall 33 is arranged along the treatment portion 56A.

The positioning portion 34 should be structured in such a manner that the imaging probe 40 is positionable. For example, it is desirable that the positioning portion 34 is structured to include a wall 34A that abuts on the outer surface of the imaging probe 40. In this case, it is possible to appropriately position the imaging probe 40 by making the imaging probe 40 abut on the wall 34A. To further enhance this effect, it is more desirable that the positioning portion 34 includes the wall 34A that abuts on the outer surface of the imaging probe 40 at different angles, and which connects the outer surface and the inner surface. The examples illustrated in FIG. 2A and FIG. 2B include the wall 34A that is abuttable on the outer surface of the imaging probe 40 from at least two directions. Therefore, it is possible to more appropriately position the imaging probe 40. Here, the expression that the wall "that abuts on the outer surface of the imaging probe at different angles" means that normals to tangent planes at two of contact points of the wall and the outer surface of the imaging probe have different angles from each other.

In the pattern illustrated in FIG. 2A, the positioning portion 34 is structured as a hole extending through the pattern 30 from the inner surface 32 to the outer surface 31, and an ultrasonic probe, as the imaging probe 40, is insertable and detachable through the hole. When the positioning portion 34 is structured as a hole, the hole may have any size as long as the imaging probe 40 is insertable and detachable through the hole. When the hole is structured in such a manner that the outer surface of the imaging probe 40 and the wall of the hole are substantially in close contact with each other, as in the embodiment of the present invention, it is possible to position the imaging probe 40 at a more appropriate position.

Alternatively, the pattern may be structured by providing the positioning portion 34 at an edge of the pattern, as illustrated in FIG. 2B. In this case, the imaging probe 40 is easily insertable and detachable. FIG. 2B illustrates an example in which the positioning portion 34 is structured as a bay-shaped portion (a recess or the like) with the wall 34A that abuts on the outer surface of the imaging probe 40 at different angles. In this case, the imaging probe 40 is easily insertable and detachable. Further, it is possible to appropriately position the imaging probe 40.

Further, an index indicating the positioning portion 34 may be provided in the positioning portion 34 or near the positioning portion 34 in such a manner that the positioning portion 34 is identifiable. In FIG. 2B, a band-shaped colored portion 34B is provided, along the guide wall 34A of of the positioning portion 34, on the outer surface 31. In this case, a user can more easily recognize the position at which the imaging probe 40 should be arranged. Alternatively, the positioning portion 34 may be structured in such a manner that the position at which the imaging probe 40 should be arranged is identifiable by using various kinds of index, such as an arrow and a character, or by using different colors. When the positioning portion 34 is structured as a hole or a recess having a sufficiently large size with respect to the imaging probe 40, it is desirable that the positioning portion 34 is structured in such a manner that the position at which the imaging probe 40 should be arranged is identifiable by using various kinds of index, such as an arrow and a character, or by using different colors.

Further, as illustrated in FIGS. 2A and 2B, the positioning portion 34 of the pattern 30 is provided at a position in which a tomographic image of cross section C of the organ including target portion A, which is a branching portion of blood vessels 6 in the liver 5, is imageable when the guide wall 33 is arranged along the treatment portion 56A.

The "target portion" should be a characteristic portion, which is usable as a mark by which a relative position with respect to an organ is recognizable. For example, a part of an anatomical structure, such as a branching point of blood vessels in the organ, a lesion region and an outline of an organ may be used as the target portion.

Further, the positioning portion 34 may position the predetermined imaging probe 40 at an arbitrary position as long as a tomographic image of cross section C of the organ including target portion A of the organ is imageable when the guide wall 33 is arranged along the treatment portion 56A on the organ (please refer to FIG. 2A). When the positioning portion 34 positions the imaging probe 40 near the treatment portion 56A, it is possible to more accurately arrange the pattern 30 at an appropriate position of the organ.

When the imaging probe 40 is positioned by the positioning portion 34, the imaging probe 40 images cross section C of the organ including target portion A. Regarding cross section C, it is desirable that relative positional relationship between target portion A and treatment portion 56A is checked in advance by using a three-dimensional image 7 of a patient or the like obtained by doctors before surgery.

According to the pattern 30 (or the pattern 30A), the position of the guide wall 33 is adjusted along the treatment portion 56A by arranging the pattern 30 (or the pattern 30A) on the surface of the organ in such a manner that a tomographic image imaged by the imaging probe 40 positioned by the positioning portion 34 includes target portion A. Therefore, it is possible to arrange the pattern 30 (or the pattern 30A) at an appropriate position on an organ.

Especially, when the organ consists of soft tissue, or the organ does not have sufficient external characteristics on its surface, it is difficult to adjust the position of the pattern 30 and the position of the organ with each other only based on external characteristics of the organ. Even in such a case, it is possible to appropriately arrange the pattern 30 (or the pattern 30A) at an appropriate position on the organ by adjusting the position of the organ and the position of the pattern 30 with each other by using a characteristic portion in the organ as a target portion.

Further, the pattern 30 may be modified in an arbitrary manner as long as the aforementioned effects are achievable. For example, the area of the pattern 30 covering the liver 5 may be set in an arbitrary manner. As long as the inner surface of the pattern 30 and the organ's outer surface partially match with each other, the inner surface of the pattern 30 may include a part that does not match with the organ's outer surface. For example, a very small uneven pattern may be provided on the inner surface of the pattern 30 as long as it can be regarded as substantially matching with the organ's outer surface. Further, the form of the outer surface of the pattern 30 may be set in an arbitrary manner. When there are plural treatment portions on an organ, plural guide walls may be provided. Further, an observation hole through which the imaging probe 40 is insertable and detachable may be provided besides the positioning portion 34. Further, plural positioning positions 34 may be provided so that target portion A is imageable from different directions. Alternatively, plural positioning positions 34 that can image plural target portions, respectively, may be provided. Further, the pattern may be composed of arbitrary material. If the pattern 30 is composed of transparent or semi-transparent material, even if the pattern is arranged on the pattern, the external appearance of the organ is recognizable, and that is desirable.

Figure 3:
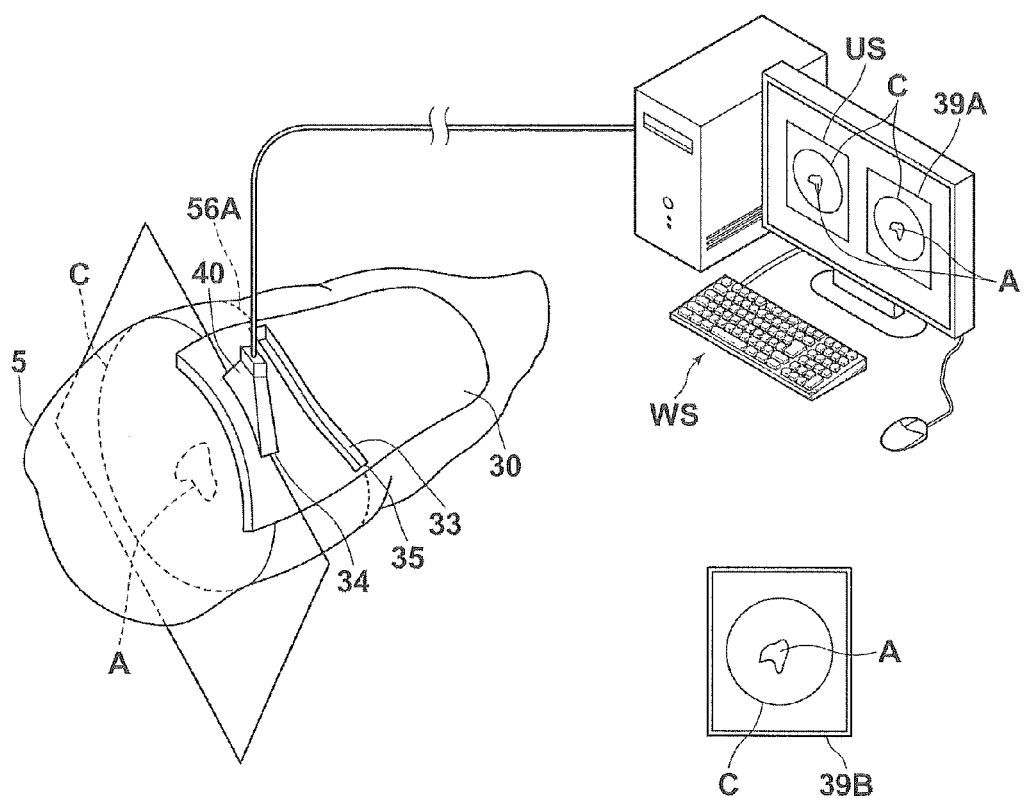
FIG. 3 is a diagram illustrating an example of a surgery support set according to an embodiment of the present invention.

Next, a surgery support set according to an embodiment of the present invention will be described. FIG. 3 is a diagram for explaining the surgery support set according to an embodiment of the present invention.

The surgery support set includes the pattern 30 (the same as the pattern 30 illustrated in FIG. 2A) and reference image 39A that has been output in such a manner that a tomographic image of cross section C of the patient's organ including target portion A is visually recognizable. In the pattern 30, the positioning portion 34 is structured in such a manner that the imaging probe 40 positioned by the positioning portion 34 can perform tomography of cross section C of the organ represented by reference image 39A when the guide wall 33 is arranged along the treatment portion 56A on the liver 5.

As illustrated in FIG. 3, according to the set of the pattern 30 and reference image 39A, doctors sequentially perform imaging by the imaging probe 40 inserted into the positioning portion 34 by moving the pattern 30 on the liver 5 while checking cross section C of the organ including target portion A in reference image 39A displayed on a display of workstation WS for surgery. Therefore, it is possible to adjust the position of the pattern 30 so that imaged image US (here, a two-dimensional ultrasonic image imaged by an ultrasonic probe) represents cross section C of the organ represented by reference image 39A. Reference image 39A represents cross section C of the organ imageable by the imaging probe 40 positioned by the positioning portion 34 when the guide wall 33 is arranged along the treatment portion 56A on the liver 5. Therefore, it is possible to arrange the pattern 30 at an appropriate position on the organ by adjusting the position of the pattern 30 on the liver 5 in such a manner that cross section C of the organ imaged by the imaging probe and cross section C of the organ represented by the reference image 39 match with each other.

Especially, when an organ consists of soft tissue, or the organ does not have sufficient external characteristics on its surface, it is difficult to adjust the position of the pattern 30 and the position of the organ with each other only based on external characteristics of the organ. Even in such a case, it is possible to adjust the position of the pattern 30 and the position of the organ with each other by comparing reference image 39A and the image imaged from the imaging probe 40. In reference image 39A, reference image 39D (image data) representing cross section C of the organ including, as target portion A, a characteristic portion in the organ is output in a visually recognizable manner. Therefore, it is possible to accurately arrange the pattern 30 (or the pattern 30A) at an appropriate position on the organ.

Here, the reference image "output in a visually recognizable manner" means a reference image displayed (output) on a display, or a reference image printed on a sheet. In the surgery support set, reference image 39B printed on a sheet may be provided instead of an image displayed on a display.

Figure 5A:
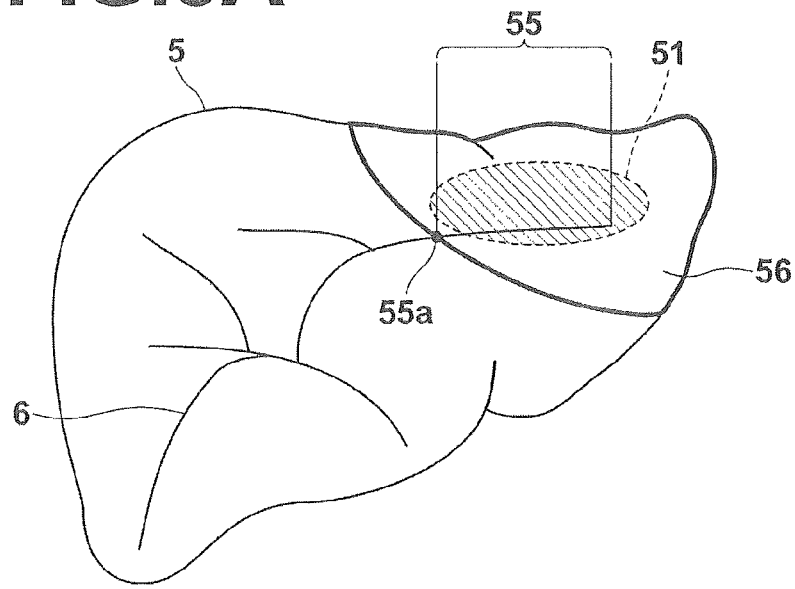
FIG. 5A is a diagram for explaining excision region determination processing according to an embodiment of the present invention.
Figure 5B:
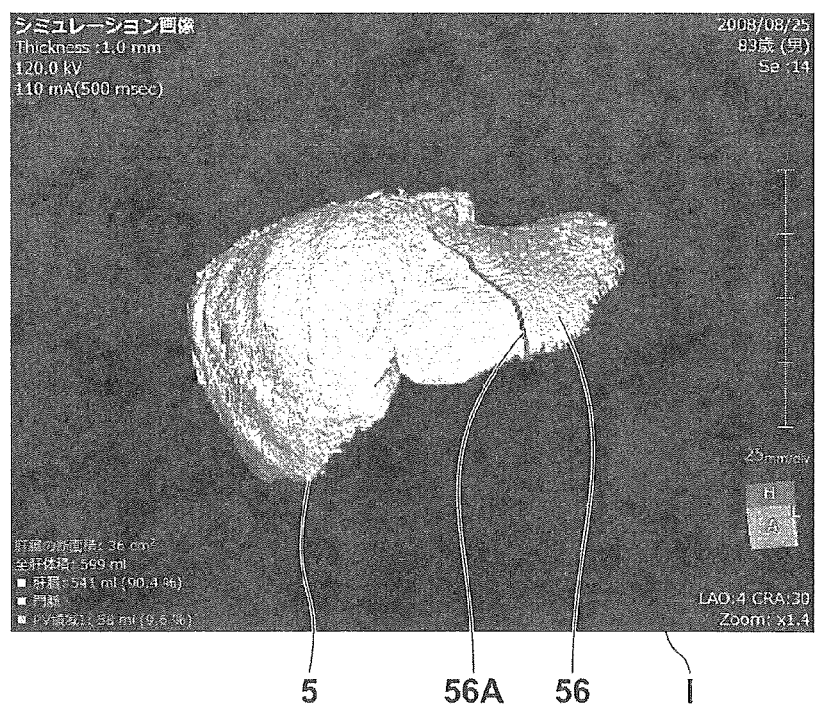
FIG. 5B is a diagram illustrating an excision region determined in an embodiment of the present invention.

FIG. 4A and FIG. 4B are flowcharts for explaining the flow of surgery support processing, which is processing for generating pattern model 30D and reference image 39D. Pattern model 30D is data of the pattern 30 according to an embodiment of the present invention, and reference image 39D is data of reference image 39A. FIG. 5A is a diagram for explaining processing for determining an excision region 56 of the liver 5 according to an embodiment of the present invention. FIG. 5B is a diagram illustrating the determined excision region 56 in the liver 5. Next, surgery support processing according to an embodiment of the present invention will be described with reference to FIG. 4A, FIG. 4B, FIG. 5A and FIG. 5B.

First, when the image obtainment unit 11 detects selection of a surgery support function according to an embodiment of the present invention in a selection menu, the image obtainment unit 11 displays a list of ID's of subjects to be examined. When the surgery support apparatus 1 detects a selection operation by a user, the surgery support apparatus 1 loads an image file related to the selected subject to be examined into a memory (S01).

Here, the image obtainment unit 11 obtains an X-ray CT image (volume data) representing the liver 5, which is an organ on which surgery is to be performed, as three-dimensional image 7 to be processed. An arbitrary known image, such as an MRI image, may be used instead of the CT image as long as the image is a three-dimensional image 7 representing an organ on which surgery is to be performed.

Then, the organ region extraction unit 12 loads the three-dimensional image 7 into a memory. First, the organ region extraction unit 12 extracts the liver 5, which is an organ region, from the three-dimensional image 7 (S02). Then, the extracted liver 5 is displayed on a display 3 by the display control unit 21.

Here, the organ region extraction unit 12 calculates a feature value representing the likelihood of an outline of a liver with respect to the value (CT value) of each voxel data constituting the three-dimensional image 7. Further, the organ region extraction unit 12 judges whether the value of the voxel represents the outline of the liver or not by evaluating the calculated feature value based on an evaluation function obtained in advance by machine learning. Then, the organ region extraction unit 12 obtains the outline of the liver based on voxels that have been judged to represent the outline of the liver. Further, the organ region extraction unit 12 obtains a surface model representing the surface form of the organ by processing voxels representing the outline of the liver by using Marching cubes. Here, the surface model representing the surface form of the organ is a model defining the surface form of the organ as a polygon composed of plural triangles, each connecting plural vertices located on the surface of the liver by edges. Any method may be adopted as a method for extracting an organ region. A method for directly extracting a surface model from a three-dimensional image by using a known method may be adopted.

Next, the lesion region extraction unit 13 extracts a lesion region 51 from the liver 5 included in the three-dimensional image 7 (S03). As illustrated in FIG. 5A, in the embodiment of the present invention, a user performs an operation for selecting a lesion region input mode from a selection menu. Further, the user specifies the lesion region 51 included in the liver region on the displayed three-dimensional image at the input unit 4. The lesion region extraction unit 13 detects such an operation performed by the user at the input unit 4, and extracts the detected region, as a lesion region 51. Various known techniques may be adopted, as the technique applicable to detection of a lesion region, as long as the technique detects a lesion included in the organ.

Meanwhile, the structure region extraction unit 14 performs blood vessel region extraction processing on the liver 5 extracted from the three-dimensional image 7, and extracts a blood vessel region 6 dominating the liver (S04). The surgery support apparatus 1 may perform the step of S03 and the step of S04 in a switched order, or in parallel.

The expression "dominating an organ" means keeping the function of the organ normal by supplying oxygen or nutrition to the organ. For example, if the organ is a liver, a blood vessel or vessels correspond to a structure dominating the organ. If the organ is a lung, a bronchus or bronchi correspond to the structure dominating the organ. If the organ is a brain, a cerebral artery corresponds to the structure dominating the organ.

Next, the dominated region extraction unit 15 extracts, based on the extracted liver 5 and the extracted blood vessel region 6, each of dominated regions, which are dominated by vascular branches constituting the blood vessel region 6, respectively (S05).

Here, the dominated region extraction unit 15 constructs a tree structure composed of vascular branches of the extracted blood vessel region 6. Further, the dominated region extraction unit 15 detects plural candidate points constituting the tree structure, and stores coordinate information about the detected plural candidate points and vector information representing the directions of vascular branches in a memory together with identifiers of the candidate points and the vascular branches. Then, the dominated region extraction unit 15 identifies the outline of a blood vessel (an outer wall of the blood vessel) in a cross section perpendicular to the path of the blood vessel for each detected candidate point based on values (CT values) of voxels surrounding the candidate point. A shape is identified by using a known segmentation technique typified by Graph-Cuts.

Further, the dominated region extraction unit 15 identifies, based on the constructed tree structure composed of vascular branches of the blood vessel region 6 and the liver region, a blood vessel dominating a region to which a region other than blood vessels in the liver region (the parenchyma of the liver) belongs by using a Voronoi diagram. Here, the dominated region extraction unit according to the embodiment of the present invention uses a technique similar to the dominated region determination technique disclosed in Japanese Unexamined Patent Publication No. 2003-033349. Further, the present invention is not limited to the embodiment of the present invention. Various other known methods may be used as long as a dominated region is determinable.

Next, as illustrated in FIG. 5A, the excision region determination unit 16 displays the blood vessel region 6 on the display 3. Further, the excision region determination unit 16 receives specification of a specified position on a blood vessel (a position at which the blood vessel should be ligated) by a user's manual operation using an input unit 4, such as a mouse. Further, the excision region determination unit 16 obtains a blood vessel part (a blood vessel partial region 55) extending from a specified position 55a in the blood vessel region 6 toward an organ-part side including the lesion region 51. Further, the excision region determination unit 16 determines, based on the extracted dominated region, the organ part dominated by the blood vessel partial region 55, and which includes the lesion region 51, as an excision region 56 (S06). The blood vessel partial region 55 may be set by using various known methods. The blood vessel partial region 55 may be automatically set by using a known technique, such as Japanese Unexamined Patent Publication No. 2001-283191.

Next, the image generation unit 19 sets a display parameter based on the three-dimensional image 7 in such a manner that the determined excision region 56 is visually recognizable. Further, the image generation unit 19 generates surface rendering image I, as illustrated in FIG. 5B (S07). Here, any image may be used instead of surface rendering image I as long as the image is obtained, based on a three-dimensional image obtained by an X-ray CT apparatus, an MRI apparatus or the like, by projecting a target region, such as an anatomical structure and a lesion region, in the three-dimensional image onto a projection plane with stereoscopic shading. For example, a volume rendering image may be used instead of surface rendering image I.

Figure 6A:
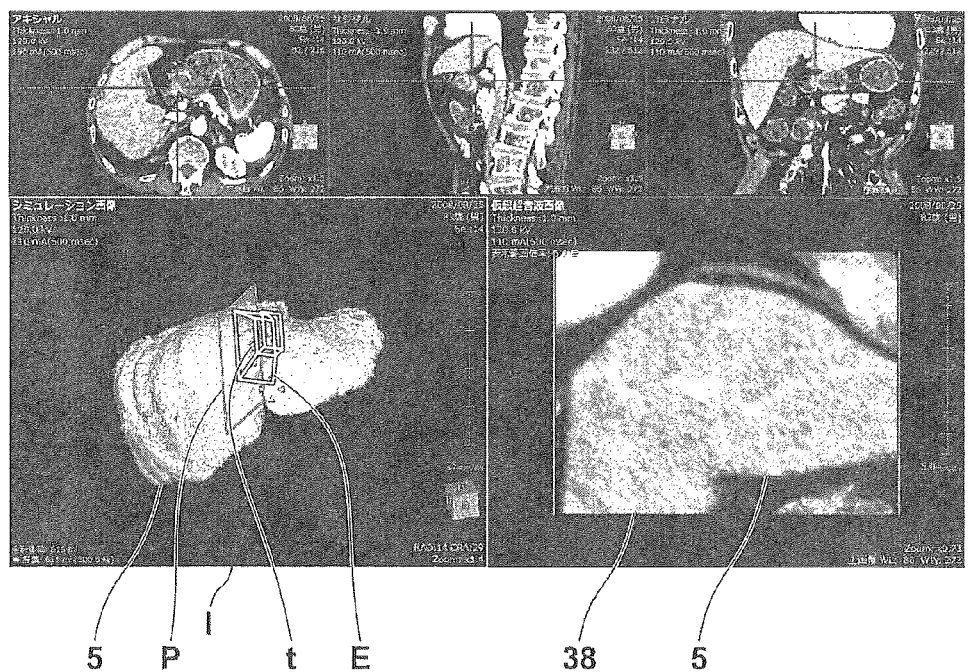
FIG. 6A is a diagram for explaining a method for determining a reference image according to an embodiment of the present invention (No. 1)
Figure 6B:
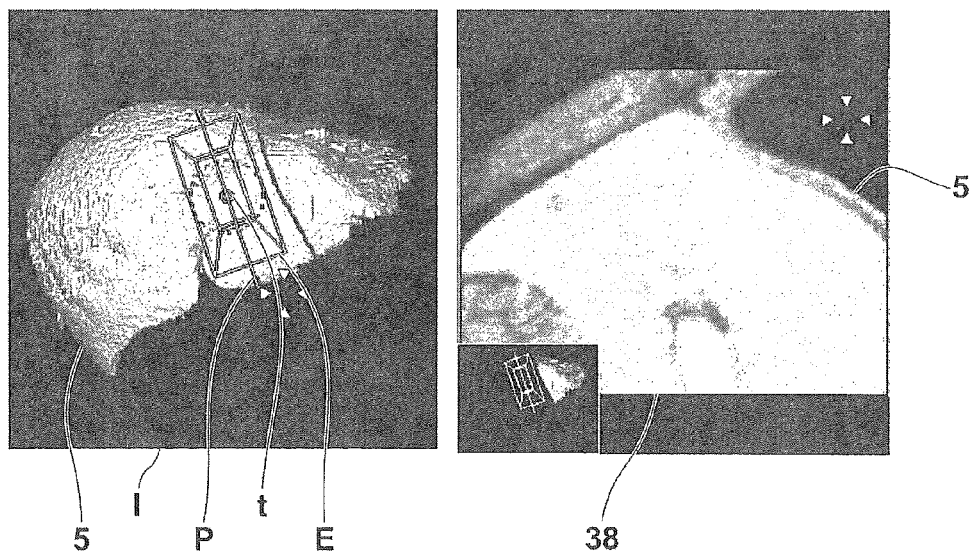
FIG. 6B is a diagram for explaining a method for determining a reference image according to an embodiment of the present invention (No. 2)

FIGS. 6A and 6B illustrate examples of screen display for determining reference image 39D (image data of a reference image). In the embodiment of the present invention, when the excision region 56 is determined, a user performs an operation for selecting a reference image determination mode from a selection menu. Then, a screen for determining reference image 39D (image data of the reference image), as illustrated in FIG. 6A or FIG. 6B, is displayed. Then, the display control unit 21 displays surface rendering image I on the display 3, as illustrated in FIG. 6A (S08). Further, the display control unit 21 displays virtual probe E, which is an index representing an ultrasonic probe, on the display. Virtual probe E is displayed on surface rendering image I in such a manner that candidate position t, which is a point included in candidate image 38, and the direction of a normal to candidate image 38 are receivable.

In FIGS. 6A and 6B, a wider surface of the quadrilateral-pyramid-like-shape of virtual probe E (hereinafter, referred to as a virtual acoustic surface) represents the form and the size of an acoustic surface of an ultrasonic probe used in surgery (a surface on which an acoustic element array is arranged).

The reference image determination unit 17 receives a user's input of rotating or moving virtual probe E at the input unit 4, such as a mouse. The reference image determination unit 17 obtains, as candidate position t, a middle point of the virtual acoustic surface of virtual probe E. Further, the reference image determination unit 17 obtains the direction of a normal to the virtual acoustic surface of virtual probe E. Then, the reference image determination unit 17 obtains the direction of a normal to candidate image 38 based on the direction of the normal to the virtual acoustic surface.

Further, it is assumed that a relative rotation amount and a relative rotation direction for matching the direction of a normal to the acoustic surface of the ultrasonic probe used in surgery and the direction of the normal to the imaging surface imaged by the ultrasonic probe have been obtained in advance. When the reference image determination unit 17 obtains the direction of the normal to the acoustic surface of the virtual probe, the reference image determination unit 17 rotates the obtained direction of the normal to the virtual acoustic surface in the relative rotation direction, which has been obtained in advance, by the relative rotation amount, which has been obtained in advance, and obtains the rotated direction, as the direction of the normal to candidate image 38.

The image generation unit 19 generates, based on obtained candidate position t and the obtained direction of the normal to candidate image 38, candidate image 38 including candidate position t from three-dimensional image 7 (S09).

The display control unit 21 displays the generated candidate image 38 on the display 3, as illustrated in FIG. 6A. Further, the display control unit 21 displays index P, representing the generated candidate image 38, on surface rendering image I (S10).

Then, the reference image determination unit 17 repeats the steps of S09 through S11 until a user's input of determining the displayed candidate image 38, as reference image 391D, is received (S11, N).

Here, the user places virtual probe E in the vicinity of the treatment portion 56A. Further, the user adjusts the direction of virtual probe E on the screen, and displays candidate image 38 in such a manner that the reference image includes a branching portion of blood vessels, which is target portion A. Further, the user performs an input of determining the displayed candidate image 38, as the reference image 39D, by double click of candidate image 38 at the input unit 4, such as a mouse. Then, the reference image determination unit 17 receives this input, and determines candidate image 38, as reference image 39D. Further, the reference image determination unit 17 obtains candidate position t of candidate image 38, as reference position t1 of reference image 39D, at which a middle point on the acoustic surface of the imaging probe 40 should be arranged. Here, processing for generating reference image 39D including target portion A may be performed by receiving a user's input as in the embodiment of the present invention. Alternatively, processing may be performed by using an arbitrary method, such as a method for automatically generating a reference image representing a cross section of an organ in which the major axis of an automatically extracted lesion (target portion) becomes the maximum. Further, as a method for receiving an input of determining reference image 39D, an arbitrary method may be used.

Meanwhile, when reference image 39D is determined (S11, Y), the treatment portion obtainment unit 18 obtains, as the treatment portion 56A to be excised (treated), a boundary line between the excision region 56 and non-excision region, which is not excised on the surface of the organ (S12).

Figure 7A:
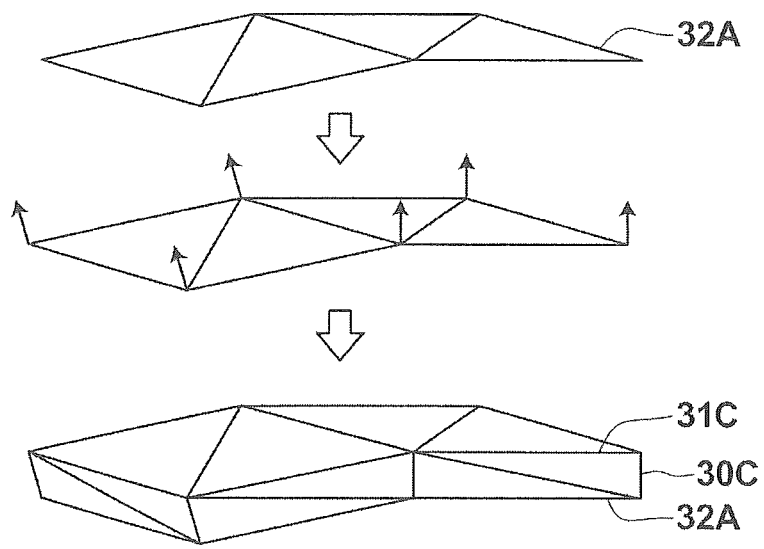
FIG. 7A is a diagram for explaining pattern model generation processing according to an embodiment of the present invention (No. 1)
Figure 7B:
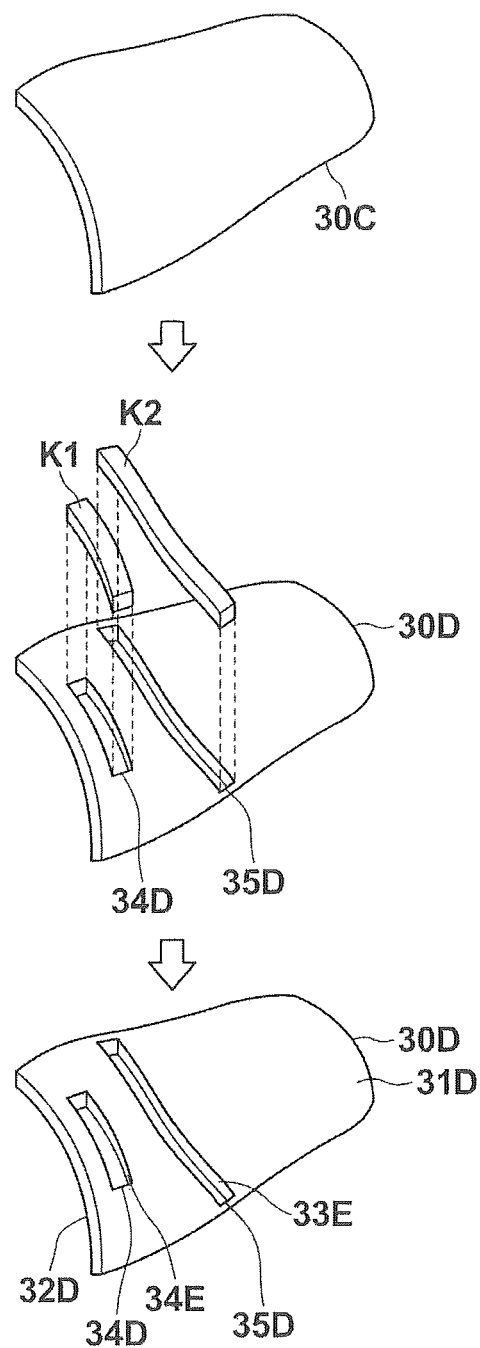
FIG. 7B is a diagram for explaining pattern model generation processing according to an embodiment of the present invention (No. 2).

Next, the pattern model generation unit 20 generates a pattern model based on the liver 5, the treatment portion 56A, reference image 39A and information about the outer surface of the imaging probe 40 obtained in advance (S13). FIGS. 7A and 7B are diagrams for explaining pattern model generation processing.

The pattern model generation unit 20 obtains an organ surface part covered by a main part of pattern model 30D. Here, the user specifies the treatment portion 56A and an organ surface part on the surface of the organ in surface rendering image I by using the input unit 4. The organ surface part is a part of the organ surface including reference position t1, and which the user wants to use as an inner surface part of pattern model 30D. Then, the pattern model generation unit 20 receives this specification, and cuts out and obtains the specified organ surface part, as the inner surface 32A of pattern model 30D, as illustrated in the upper section of FIG. 7A.

Then, as illustrated in the middle section of FIG. 7A, the pattern model generation unit 20 sets a new vertex away from each of vertices constituting the inner surface 32A of pattern model 30D. The new vertex is away by a predetermined distance in the direction of a normal to the surface of the organ at each of the vertices constituting the inner surface 32A.

Further, as illustrated in the lower section of FIG. 7A, the pattern model generation unit 20 generates the outer surface 31C of pattern model 30D by connecting the new vertices in triangle by edges. Further, the pattern model generation unit 20 generates a side wall of pattern model 30D by connecting vertices located at an edge of the outer surface 31C and vertices located at an edge of the inner surface 32A in triangle. Accordingly, a provisional main part 30C of pattern model 30D is generated.

Then, the pattern model generation unit 20 generates, based on the treatment portion 56A, polygon K2 having a form corresponding to the guide hole 35D (corresponding to the guide hole 35 in FIG. 2A) including the treatment portion 56A. Here, the pattern model generation unit 20 generates polygon K2 including an inner surface having a form corresponding to the inner surface of the provisional main part 30C, an outer surface having a form corresponding to the outer surface of the provisional main part 30C, walls (having forms corresponding to guide walls 33A and 33B) away by a predetermined distance that has been set in advance in a direction away from the treatment portion 56A, and the walls extending for predetermined lengths along the treatment portion 56A, and walls that connect the walls and extend in a short-side direction.

Further, the pattern model generation unit 20 generates polygon K1 having a form corresponding to the positioning portion 34D. Here, as illustrated in FIG. 2A, the pattern model generation unit 20 sets the positioning portion 34D, as a hole substantially in close contact with the imaging probe 40 when the imaging probe 40 is arranged in such a manner that reference position t1 is located at the center of the virtual acoustic surface. The pattern model generation unit 20 generates polygon K1 including an inner surface having a form corresponding to the inner surface of the provisional main part 30C, an outer surface having a form corresponding to the outer surface of the provisional main part 30C, and a surrounding wall substantially in close contact with the outer surface of the imaging probe 40. The pattern model generation unit 20 deletes polygon K1 having a form corresponding to the positioning portion 34 and polygon K2 having a form corresponding to the guide hole 35D from the provisional main part 30C. Accordingly, it is possible to generate pattern model 30D. Here, the guide hole 35D illustrated in FIG. 7B corresponds to the guide hole 35 illustrated in FIG. 2A. The guide wall 33E corresponds to the guide wall 33A illustrated in FIG. 2A. The positioning portion 34D illustrated in FIG. 7B corresponds to the positioning portion 34 illustrated in FIG. 2A. The wall 34E of the positioning portion illustrated in FIG. 7B corresponds to the wall 34A illustrated in FIG. 2A.

Here, the generated pattern model 30D is generated as a pattern model including the outer surface 31D, the inner surface 32D having a surface form along the organ's outer surface, the guide wall 33E connecting the outer surface 31D and the inner surface 32D along the treatment portion 56A, and the positioning portion 34D. The positioning portion 34D positions the predetermined imaging probe 40 in such a manner that a tomographic image of cross section C of the organ including target portion A of the organ is imageable when the guide wall 33E is arranged along the treatment portion 56A on the organ. The generated pattern model 30D is pattern data corresponding to the pattern 30 illustrated in FIG. 2A.

The pattern model generation unit 20 may generate a pattern model based on a user's input and required conditions by constructing the form and the size of the positioning portion 34D in an arbitrary manner. The positioning portion 34D may be a hole, a recess, a part of an edge, or the like. Further, the pattern model generation unit 20 may generate the pattern model based on a user's input and required conditions by constructing the margin width of the guide hole 35D with respect to the treatment portion 56A (a distance of the guide wall 33E with respect to the treatment portion 56A or the like), a position or a range of providing the guide wall 33E with respect to the treatment portion 56A, the number of guide walls 33E or the like in an arbitrary manner.

After then, an output unit 22 outputs (print outs) reference image 39D to a printer 9, and generates reference image 39B, which is visually recognizable as described already (S14). The generated reference image 39B may be used as reference image 39B constituting the aforementioned surgery support set.

The output unit 22 outputs pattern model 30D to a three-dimensional printer 8, and generates the aforementioned pattern (S15). Accordingly, the aforementioned pattern 30, as illustrated in FIG. 2A, is generated. The step of S15 may be performed in arbitrary timing as long as the step is performed after the step of S13 is finished. The step of S15 may be performed after an interval. Further, the step of S14 and the step of S15 may be performed in a switched order.

Further, the step of S14 may be omitted. The step of S14 may be performed in arbitrary timing as long as the step is performed after determination of reference image 39D.

According to the surgery support apparatus 1, it is possible to appropriately generate the pattern 30 based on the generated pattern model 30D.

The surgery support apparatus 1 includes the image generation unit 19 that generates a reference image 39D, which is a tomographic image of cross section C of an organ including a target portion of the organ, from a three-dimensional image 7. Therefore, it is possible to appropriately generate reference image 39D and pattern model 30D, and to appropriately produce the surgery support set based on them. Reference image 39D generated by the image generation unit 19 represents cross section C of the organ imageable by the imaging probe 40 positioned in the positioning portion 34 when the guide wall 33 is arranged along the treatment portion 56A on the liver 5. Therefore, the position of the pattern 30 is adjusted on the liver 5 in such a manner that cross section C of the organ imaged by the imaging probe 40 and cross section C of the organ represented by reference image 39B (or reference image 39A) match with each other by using reference image 39B (or reference image 39A), obtained by outputting reference image 39D in a visually recognizable manner, and the pattern 30. Accordingly, it is possible to arrange the pattern 30 at an appropriate position on the organ.

The pattern model generation apparatus further includes the reference image determination unit 17, which determines a reference image from plural candidate images 38, and the display control unit 21, which displays the reference image on a display device. The image generation unit 19 generates, based on the three-dimensional image 7, plural candidate images 38, which are tomographic images representing different cross sections of the organ, respectively. The display control unit 21 displays the generated plural candidate images 38 on the display device. The reference image determination unit 17 receives user's specification of determining the displayed candidate image 38 as reference image 39D, and thereby determines the specified candidate image 38, as reference image 39D. Therefore, it is possible to utilize the judgment by the user, and to determine reference image 39D that appropriately represents target portion A. Further, it is possible to arrange the positioning portion 34D at an appropriate position, at which cross section C of the organ represented by reference image 39D, which appropriately represents the target portion A, is imageable. Therefore, the position of the pattern 30 generated based on pattern model 30D is adjusted on the liver 5 in such a manner that cross section C of the organ imaged by the imaging probe 40 and cross section C of the organ represented by reference image 39D match with each other. Accordingly, it is possible to arrange the pattern 30 at an appropriate position on the organ.

Regarding the pattern 30, the imaging probe 40 positioned in the positioning portion 34 is an ultrasonic probe. Therefore, it is possible to appropriately position the pattern by using an imaging apparatus widely used in actual surgery. Further, the present invention is not limited to the embodiments of the present invention. In the present invention, the imaging probe may be an imaging probe of any kind of imaging apparatus as long as it is an imaging probe of an imaging apparatus that can obtain an image of a cross section of an organ in which a target portion of the organ is observable. The imaging probe may have various kinds of shape.

Further, in each of the aforementioned embodiments, the surgery support apparatus 1 is a single computer in which each of the programs has been installed. Alternatively, the programs may be installed in plural computers in a distributed manner to configure a surgery support system that can achieve a function similar to the function of the surgery support apparatus 1. For example, data of a pattern or a reference image may be recorded on a medium, such as a CD-R and a DVD, and the data of the pattern or the reference image may be copied into another computer through the media in which the data of the pattern or the reference image are recorded or through a network. Further, the pattern or the reference image may be output from the other computer.

In each of the embodiments, the surgery support apparatus 1 may include a unit for performing output of a print and output of data (recording on a medium, such as a CD-R and a DVD, and transfer through a network) in addition to output of data on a display. In other words, in the present invention, the manner of outputting index values is not limited to output of data on a display.

Each of the embodiments illustrates processing performed when the organ is the liver 5 and target portion A is a branching point of portal veins. However, the present invention is not limited to supporting surgery of a liver. The present invention may be applied also to supporting surgery of a different organ, such as a lung.

The present invention is not limited to the aforementioned embodiments. The present invention may be modified in various manners without departing from the gist of the present invention.

What is claimed is:

1. A surgery support apparatus comprising:
 a processor; and
 a memory, the memory storing instructions to cause the processor to:
  obtain a three-dimensional image representing a patient's organ;
  extract the organ from the three-dimensional image;
  obtain a treatment portion, at which desirable treatment for the organ is performed, on a surface of the organ;
  generate, based on the extracted organ and the obtained treatment portion, a pattern model including an outer surface, an inner surface having a surface form along an organ's outer surface of the organ, a guide wall connecting, along the treatment portion, the outer surface and the inner surface, and a positioning portion that positions a predetermined imaging probe;
  generate, based on the three-dimensional image, a plurality of candidate images, comprising tomographic images representing different cross sections of the organ, respectively;
  display the generated plurality of candidate images on a display device; and
  determine, as a reference image, a candidate image specified by a user by receiving a specification of determining the displayed candidate image as the reference image by the user,
 wherein the memory further stores instructions to cause the processor to display images imaged from the imaging probe and the reference image together on the display device, and
 wherein a position of the positioning portion is determined in such a manner that a tomographic image of a cross section corresponding to the reference image is imaged by the imaging probe positioned at the positioning portion when the guide wall is arranged along the treatment portion on the organ.

2. The surgery support apparatus, as defined in claim 1, wherein the positioning portion includes a wall that abuts on an outer surface of the imaging probe at different angles, and that connects the outer surface and the inner surface.

3. The surgery support apparatus, as defined in claim 2, wherein the positioning portion comprises a hole extending through the pattern model from the outer surface to the inner surface, and through which the imaging probe is insertable and detachable.

4. The surgery support apparatus, as defined in claim 1, wherein the pattern model includes a guide hole extending through the pattern model from the outer surface to the inner surface, and the guide hole including the guide wall provided on both sides of the treatment portion.

5. The surgery support apparatus, as defined in claim 1, wherein the guide wall is provided on an edge of the pattern model.

6. The surgery support apparatus, as defined in claim 1, wherein the imaging probe comprises an ultrasonic probe.

7. The surgery support system apparatus, as defined in claim 1, further comprising:
 an output unit that outputs the reference image to a printer.

8. The surgery support apparatus, as defined in claim 1, wherein a position of the pattern model is adjusted on the patient's organ in such a manner that the cross section of the patient's organ imaged by the imaging probe and the cross section of the organ represented by the reference image match with each other.

9. A surgery support method performed by a surgery support apparatus, the method comprising:
 image obtainment to obtain a three-dimensional image representing a patient's organ;
 organ extraction to extract the organ from the three-dimensional image;
 treatment portion obtainment to obtain a treatment portion, at which desirable treatment for the organ is performed, on a surface of the organ; and
 pattern model generation to generate, based on the extracted organ and the obtained treatment portion, a pattern model including an outer surface, an inner surface having a surface form along an organ's outer surface of the organ, a guide wall connecting, along the treatment portion, the outer surface and the inner surface, and a positioning portion that positions a predetermined imaging probe, the method further comprising:
 generating, based on the three-dimensional image, a plurality of candidate images, comprising tomographic images representing different cross sections of the organ, respectively;
 displaying the generated plurality of candidate images on a display device; and
 determining, as a reference image, a candidate image specified by a user by receiving a specification of determining the displayed candidate image as the reference image by the user,
 wherein the displaying displays images imaged from the imaging probe and the reference image together on the display device, and
 wherein a position of the positioning portion is determined in such a manner that a tomographic image of a cross section corresponding to the reference image is imaged by the imaging probe positioned at the positioning portion when the guide wall is arranged along the treatment portion on the organ.

10. A non-transitory computer-readable storage medium having stored therein a surgery support program for causing a computer to function as:
   an image obtainment unit that obtains a three-dimensional image representing a patient's organ;
   an organ extraction unit that extracts the organ from the three-dimensional image;
   a treatment portion obtainment unit that obtains a treatment portion, at which desirable treatment for the organ is performed, on a surface of the organ;
   a pattern model generation unit that generates, based on the extracted organ and the obtained treatment portion, a pattern model including an outer surface, an inner surface having a surface form along an organ's outer surface of the organ, a guide wall connecting, along the treatment portion, the outer surface and the inner surface, and a positioning portion that positions a predetermined imaging probe;
   an image generation unit that generates, based on the three-dimensional image, a plurality of candidate images, comprising tomographic images representing different cross sections of the organ, respectively;
   a display control unit that displays the generated plurality of candidate images on a display device; and
   a reference image determination unit that determines, as a reference image, a candidate image specified by a user by receiving a specification of determining the displayed candidate image as the reference image by the user,
   wherein the display control unit displays images imaged from the imaging probe and the reference image together on the display device, and
   wherein a position of the positioning portion is determined in such a manner that a tomographic image of a cross section corresponding to the reference image is imaged by the imaging probe positioned at the positioning portion when the guide wall is arranged along the treatment portion on the organ.

* * * * *